United States Patent [19]

Moroni

[11] Patent Number: 4,567,125
[45] Date of Patent: Jan. 28, 1986

[54] ELECTROPHOTOGRAPHIC RECORDING MATERIAL

[75] Inventor: Wilko Moroni, Heidelberg, Fed. Rep. of Germany

[73] Assignee: Hoechst Aktiengesellschaft, Frankfurt am Main, Fed. Rep. of Germany

[21] Appl. No.: 558,582

[22] Filed: Dec. 6, 1983

[30] Foreign Application Priority Data

Dec. 9, 1982 [DE] Fed. Rep. of Germany ....... 3246036

[51] Int. Cl.$^4$ .......................... G03G 5/14; G03G 5/06
[52] U.S. Cl. ....................................... 430/58; 430/59; 430/96
[58] Field of Search ....................... 430/58, 59, 76, 78, 430/83, 96

[56] References Cited

U.S. PATENT DOCUMENTS

| | | | |
|---|---|---|---|
| 3,837,851 | 9/1974 | Shattuck et al. | 430/59 |
| 3,904,407 | 9/1975 | Regensburger et al. | 430/58 |
| 3,992,205 | 11/1976 | Wiedemann | 430/58 |
| 4,150,987 | 4/1979 | Anderson et al. | 430/59 X |
| 4,278,746 | 7/1981 | Goto et al. | 430/59 |
| 4,278,747 | 7/1981 | Muragama et al. | 430/59 X |

Primary Examiner—Roland E. Martin
Attorney, Agent, or Firm—Schwartz, Jeffery, Schwaab, Mack, Blumenthal & Evans

[57] ABSTRACT

The invention describes an electrophotographic recording material made of an electrically conductive support and at least one binder-containing photoconductive layer which contains (1) a perylenetetracarboxylic acid derivative as a compound which produces charge carriers and (2) a hydrazone or pyrazoline derivative as a compound which transports charges, wherein the compound which produces charge carriers is a diimide of perylenetetracarboxylic acid and the charge-transporting compound has the general formula

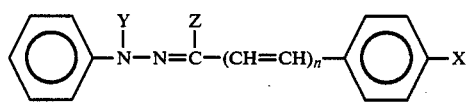

in which
X denotes methyl or methoxyl,
n denotes zero or 1,
Y denotes phenyl and
Z denotes hydrogen, or
Y and Z together denote a grouping of the formula

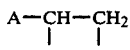

where A denotes phenyl or p-tolyl.

11 Claims, 5 Drawing Figures

ELECTROPHOTOGRAPHIC RECORDING MATERIAL

BACKGROUND OF THE INVENTION

The present invention relates to an electrophotographic recording material made of an electrically conductive support and at least one binder-containing photoconductive layer which contains a perylenetetracarboxylic acid derivative, as a compound which produces charge carriers, and a hydrazone or pyrazoline derivative, as a compound which transports charges.

It is known (German Offenlegungsschrift No. 2,919,791, corresponding to U.S. Pat. No. 4,278,747) to use electrophotographic recording materials which contain, in the organic photoconductor layer, a very wide variety of hydrazone compounds having an aromatic hydrocarbyl group or an aromatic heterocyclic group. The photoconductor layer can additionally contain dyestuffs and/or electron acceptors which form a charge transfer complex with the hydrazone compound. It can also be combined with such materials as selenium, selenium compounds, cadmium sulfide, phthalocyanine pigment, perinone or perylene pigment, or bisazo and cyanine pigment.

It is also known (U.S. Pat. No. 4,030,923, corresponding to German Offenlegungsschrift No. 2,654,873) to use an electrophotographic recording material in which a photoconductor layer contains triarylpyrazoline in conjunction with binder mixtures as a charge transport layer. Highly abrasion-resistant materials are obtained when polycarbonates combined with bisazo pigments are used as binders.

It is further known (German Pat. No. 2,924,865, corresponding to U.S. Pat. No. 4,278,746) to use, in electrophotographic recording materials with a conductive support, binder-containing charge transport layers incorporating pyrazoline compounds which can be combined with a very wide variety of substances producing charge carriers and with polymeric binders. It is also known (U.S. Pat. No. 3,904,407, and German Offenlegungsschrift No. 2,237,539, corresponding to U.S. Pat. No. 3,871,882) to use, in photoconductive systems, perylene pigments, in particular perylenetetracarboxylic acid derivatives, as compounds which produce charge carriers. Perylene pigments are also known from U.S. Pat. No. 3,972,717. German Offenlegungsschrift No. 3,019,326 reveals the use of a certain crystal modification of the N,N'-bis-(3-methoxypropyl)-diimide of perylenetetracarboxylic acid.

The known recording materials are highly light-sensitive, particularly in a photoconductor double-layer arrangement of a layer producing charge carriers and a charge transport layer. Their mechanical resistance properties are additionally promoted by using compatible high-polymeric binders. For instance, vacuum-deposited layers of perylenetetracarboxylic acid derivatives can be combined with charge transport layers which contain polyester or cellulose-ester binders. These recording materials, although highly light-sensitive, are somewhat brittle, leading to fine hairline cracks in the layers, or they are not sufficiently abrasion-resistant. If, however, impact-resistant, highly abrasion-resistant polycarbonates or polyepoxides are incorporated in corresponding recording materials, either the good photoconductivity of the latter decreases or there evidently are incompatibility phenomena which disqualify the recording material from practical use in cyclic copying processes.

It is true that the known state of the art makes it possible, all in all, to obtain highly light-sensitive electrophotographic recording materials that are sensitive to relatively long wavelengths. Nevertheless, this sensitivity to relatively long wavelengths, as, for example, in the case of bisazo pigments, has to be filtered out again for office copiers in order to obtain practically correct color reproduction of the originals. It is regarded as a further disadvantage that photoconductor layers of this type can only be prepared in a double-layer arrangement when the layer containing the compound which produces the charge carriers is in a dispersion with a binder, since bisazo pigments will decompose if applied at elevated temperatures.

SUMMARY OF THE INVENTION

It is therefore the object of the present invention to provide a highly light-sensitive electrophotographic recording material which is extremely abrasion-resistant and adheres firmly to a conductive support. In accomplishing the foregoing object, there has been provided, in accordance with one aspect of the present invention, an electrophotographic recording material comprising an electrically conductive support and at least one binder-containing photoconductive layer comprising a binder and a charge carrier-producing composition comprising a diimide of perylenetetracarboxylic acid, and a charge-transporting composition comprising a compound of the formula

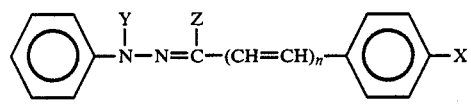

in which
X denotes methyl or methoxyl,
n denotes zero or 1,
Y denotes phenyl and
Z denotes hydrogen, or
Y and Z together denote a grouping of the formula

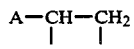

where A denotes phenyl or p-tolyl.

Other objects, features, and advantages of the present invention will be apparent from the following detailed description of preferred embodiments, considered with the attached figures.

DETAILED DESCRIPTION OF PREFERRED EMBODIMENTS

Figure 1:
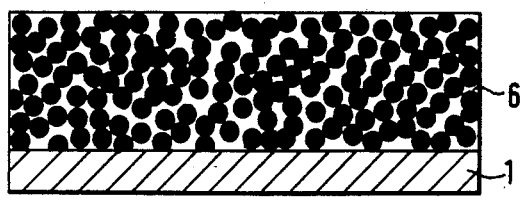
FIG. 1 shows one embodiment of the present invention wherein an electrically conductive layer support carries a photoconductive layer comprising a dispersion of charge-transporting compound and charge-producing compound in a binder.
Figure 2:
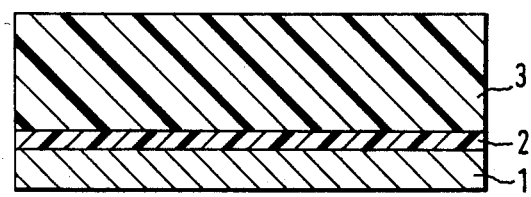
FIG. 2 shows another embodiment having a double-layer configuration, wherein one layer contains a compound which produces charge carriers and a second layer is the charge transport layer.
Figure 3:
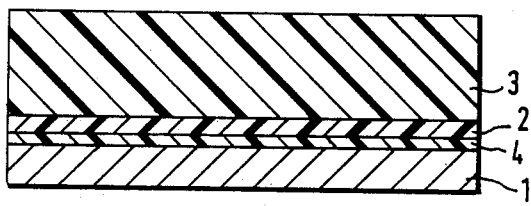
FIG. 3 shows a second double-layer embodiment which includes an insulating interlayer.
Figure 4:
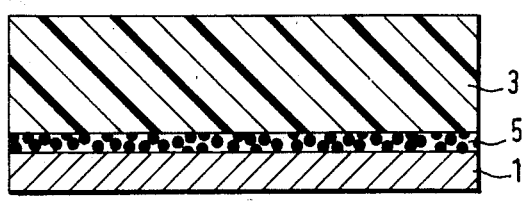
FIGS. 4 and 5 show other embodiments wherein a charge transport layer and a layer comprising a dispersion of a charge carrier-producing compound in a binder are included.
Figure 5:
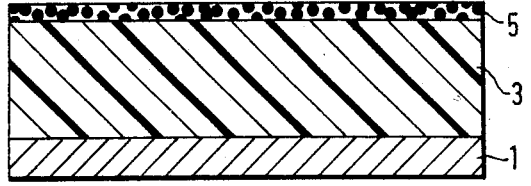

According to the invention, compounds which produce charge carriers can be N,N'-dimethylperylene-3,4,9,10-tetracarboxylic acid diimide (formula A), N,N'-bis-(3-methoxypropyl)-perylene-3,4,9,10-tetracarboxylic acid diimide (formula B), and the condensation product of perylenetetracarboxylic anhydride and o-phenylenediamine (formula C). The formulas are shown below.

The compounds are known and can be prepared and used by the methods described in German Offenlegungsschrift No. 2,237,539, German Offenlegungsschrift No. 3,019,326, and U.S. Pat. No. 3,972,717, the teachings of which are incorporated herein. The compounds are preferably vacuum-deposited onto the support.

According to the invention, the charge-transporting compounds can be 1,5-diphenyl-3-p-methoxyphenyl-pyrazoline (formula 1), 1-phenyl-3-p-methylstyryl-5-p-tolyl-pyrazoline (formula 2), the condensation product of 1,1-diphenylhydrazine and anisaldehyde (formula 3), and/or the condensation product of 1,1-diphenylhydrazine and p-tolylaldehyde (formula 4). These formulas are also shown below.

I

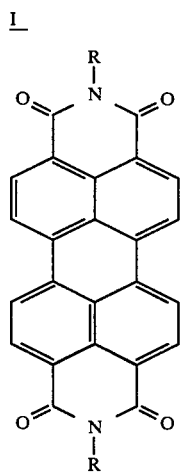

R = CH₃  A
R = (CH₂)₃OCH₃  B

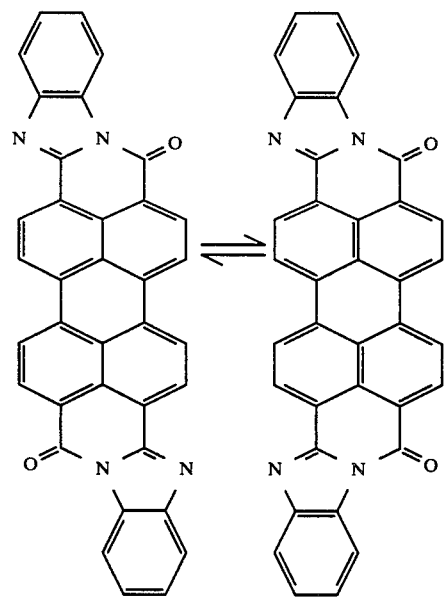

C

II

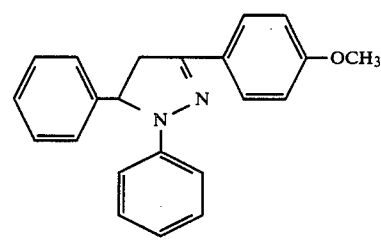

1

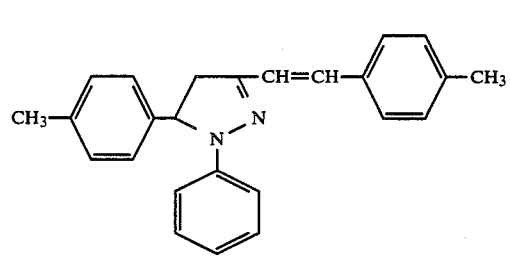

2

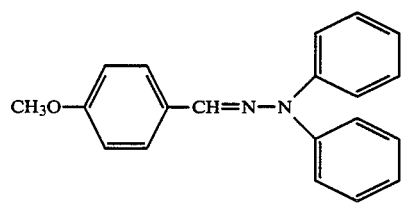

3

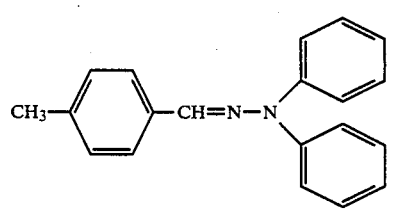

4

The pyrazoline compounds are prepared in accordance with the methods described in German Auslegeschrift No. 1,060,714 (corresponding to U.S. Pat. No. 3,180,720) at page 1, and the condensation of the hydrazines is described in German Offenlegungsschrift No. 2,919,791 (corresponding to U.S. Pat. No. 4,278,747) at page 8.

The invention has the effect of matching in a most suitable way, the electronic potentials and configurations of charge-transporting compounds, with the spectrally particularly advantageous perylenetetracarboxylic acid diimides, producing charge carriers by affecting the $\pi$-electron system of the hydrazone and pyrazoline compounds according to the invention through, appropriately, electron-attracting or electron-donating substituents. It has been found, according to the invention, that only charge-transporting compounds which are substituted in a very well-defined way produce, in conjunction with a binder, highly light-sensitive photoconductor layers for electrophotographic recording materials with the perylenetetracarboxylic acid diimides. The advantages of perylenetetracarboxylic acid diimides with respect of their preparation, spectral sensitivity, vapor deposition, and dispersibility have been disclosed by the above-mentioned publications.

The surfaces of the recording materials according to the invention can be made to be highly abrasion-resistant and highly adhesive, attaining $E_{\frac{1}{2}}$ values of less than 2.5 $\mu J/cm^2$.

The structure of the electrophotographic recording material according to the invention will now be schematically illustrated in more detail by means of FIGS. 1 to 5, which show various embodiments of the claimed invention. In the figures, layer 1 is the electrically conductive support, layer 2 is the layer which produces charge carriers, and layer 3 is the charge transport layer. Layer 4 is an insulating interlayer, and layer 5 is a layer containing a charge carrier-producing compound which is dispersed in a binder. Layer 6 is a photoconductive layer comprising a dispersion of a charge-transporting compound, a charge-generating compound, and a binder, a.s.o.

The insertion of an insulating interlayer, which can be a thermally, anodically, or chemically-produced aluminum oxide interlayer (FIG. 3, layer 4), has the aim of reducing the extent of charge carrier injection in the dark from the metal into the photoconductor layer. On the other hand, it should not impair the charge flux during exposure. The interlayer acts as a barrier layer. The interlayer can also function to improve the adhesion between the surface of the support and the charge-carrier-generating or the photoconductive layer.

Various natural or synthetic resin binders can be used for the interlayer, but it is preferable to use materials which adhere firmly to a metal surface, specifically an aluminum surface, and which are not excessively swelled as further layers are subsequently applied. They include polyamide resins, polyvinylphosphonic acid, polyurethanes, polyester resins, and specifically alkali-soluble binders, such as, for example, styrene/maleic anhydride copolymers.

The organic interlayers can be up to 5 $\mu m$ thick, while an aluminum oxide interlayer is generally within the range from 10 nm to 5 $\mu m$.

The monodispersion layer arrangement according to FIG. 1 of a given pigment/photoconductor/binder system is in principle the least light-sensitive, since here the trapping action for the charge carriers produced is greatest. However, the arrangement of layers also determines the polarity of the charge. While monodispersed layers as shown in FIG. 1 can be charged both positively and negatively, layers in double layer arrangements with p-photoconductors (FIGS. 2, 3, and 4) can only be charged negatively, and those in an inverse arrangement (FIG. 5) can only be charged positively.

The monodispersion layer arrangement according to FIG. 1 is advantageous for the electrophotographic production of printing forms, while a multilayer arrangement has advantageous properties for cyclic processes, for example, in copiers.

The electrically conductive support used is preferably aluminum foil or transparent, aluminum vapor deposited or aluminum-clad polyester film, but any other support which has been made sufficiently conductive can be used. The photoconductive layer can also be arranged on a drum, on flexible endless belts made, for example, of nickel or steel or the like, or on plates.

A layer containing the charge-transporting compound and binder but no perylenetetracarboxylic acid diimide has virtually no sensitivity to light in the visible region (420–750 nm). Only on addition of perylene pigment will the photons of the light produce excited electron states in the pigment and, under the influence of the electric field, produce charge carriers which are transported through the layer by the molecules of the charge transport compound.

In the dark the electrophotographic recording material has a high electrical resistance of more than $10^{12}$ $\Omega \cdot cm$. In the dark it prevents the electrostatic charge from flowing off. The discharge is only effected through the action of light.

In addition to the compounds which, according to the invention, produce charge carriers and the charge-transporting compounds, the added binder affects not only the mechanical properties of the recording material, such as abrasion, flexibility, film-formation and the like, but also, to a certain degree, the recording material's electrophotographic properties, such as light-sensitivity, residual charge and cyclic behavior.

Binders used are film-forming compounds, such as polyester resins, polyvinyl chloride/polyvinyl acetate copolymers, styrene/maleic anhydride copolymers, polycarbonates, silicone resins, polyurethanes, sulfonylurethanes, epoxy resins, acrylates, polyvinyl acetates, and polystyrenes. Successful use is also made of thermally post-crosslinking binder systems, such as reactive resins which are composed of an equivalent mixture of hydroxyl-containing polyesters or polyethers and polyfunctional isocyanates, polyisocyanate-crosslinking acrylate resins, melamine resins, unsaturated polyester resins, and the like.

The use of polycarbonates is particularly preferable, because they are highly light-sensitive, very flexible and, in particular, very abrasion-resistant.

The mixing ratio of charge-transporting compound to the binder can vary between relatively well-defined limits dictated by the demands to maximize light-sensitivity, which favor a very high proportion of charge-transporting compound, and the demands to avoid crystallization and increase flexibility, which favor a very high proportion of binders. It has been found in general that a mixing ratio of about 1:1 parts by weight is preferred, but ratios between 4:1 to 1:2 are also suitable.

A copier's respective requirements of the electrophotographic and mechanical properties of the recording material can be flexibly met by adjusting the layers in various ways, for example, through the viscosity of the binders or the proportion of charge-transporting compound.

Optimum light-sensitivity depends also on the thickness of the layer; a thickness between about 3 and 20 μm is generally used. A thickness range from 4 to 12 μm has been found to be particularly advantageous. Nevertheless, if a copier's mechanical requirements and its electrophotographic parameters (charge and developing station) allow it, the specified limits can be extended upward or downward on a case-by-case basis.

The arrangement of layers used for recording material within the present claims is immaterial to the assessment of the charge-transporting compounds and the compounds which produce charge carriers. In other words, the compounds can be used to advantage in all the layer arrangements shown in FIGS. 1 to 5. The invention will be illustrated by reference to examples in the double-layer arrangement of FIG. 2, without being limited thereto.

As the examples show, hydrazone and pyrazoline compounds of formulas 1 to 4 according to the invention are excellent charge-transporting compounds.

The light-sensitivity is measured as follows:

To determine its photosensitivity by photoptic discharge curves, the sample is moved, on a turning table, through a charge device to an exposure station where it is continuously exposed to the light from an Osram XBO 150 xenon lamp. A heat absorption glass and a 12% transparency neutral filter have been placed in front of the lamp. The intensity of light in the plane of measurement is within the range from 50 to 100 μW/cm$^2$; it is measured with an optometer immediately after determination of the photoinduced light-decay curve. The charge level and the photoinduced light-decay curve are oscillographically recorded by means of a transparent sensor via an electrometer. The photoconductive layer is characterized by the charge level ($U_o$) and the time ($T_{\frac{1}{2}}$) by which half the charge ($U_{o/2}$) has been reached. The product of $T_{\frac{1}{2}}$ and the measured intensity of light I [μW/cm$^2$] is the half-value energy $E_{\frac{1}{2}}$ [μJ/cm$^2$]. $U_R$ indicates the residual charge still left after a 0.1 second exposure.

EXAMPLE 1

N,N'-Dimethylperylene-3,4,9,10-tetracarboxylic acid diimide (formula A), the spectral light absorption of which extends from 430 to about 600 nm, is vapor-deposited under $1.33 \times 10^{-7}$ to $10^{-8}$ bar and at about 280° C. in a vacuum vapor deposition unit onto an aluminum-sputtered polyester film. The homogeneously deposited layer weighs about 150 mg/m$^2$ and completely covers the support.

The sputtered layer is whirler-coated with a solution of equal parts by weight of the hydrazone of formula 3 and of a polycarbonate resin (Makrolon 2045, Bayer) in tetrahydrofuran (THF). The layer is dried in a circulating air cabinet at about 110° C. in the course of about 5 minutes. The layer is smooth and firmly adherent. Light-sensitivity is determined by means of the characterizing method described above as being:

| (−) $U_o$ (V) | (−) $U_R$ (V) | $E_{\frac{1}{2}}$ |
|---|---|---|
| 733 | 186 | 1.15 |
| 560 | 140 | 1.35 |

If under otherwise identical conditions the hydrazone is replaced by the compounds 2-vinyl-4-(2'-chlorophenyl)-5-(4'-diethylaminophenyl)-1,3-oxazole or 2-phenyl-4-(2'-chlorophenyl)-5-(4'-diethylaminophenyl)-1,3-oxazole, as described in German Pat. No. 1,120,875 (corresponding to U.S. Pat. No. 3,257,203), or 2,5-bis-(4'-diethylaminophenyl)-1,3,4-oxadiazole, as described in German Pat. No. 1,058,836 (corresponding to U.S. Pat. No. 3,189,447), the following values are obtained:

| (−) $U_o$ (V) | (−) $U_R$ (V) | $E_{\frac{1}{2}}$ |
|---|---|---|
| 747 |  | >30 |
| 560 | 180 | 2.56 |
| 620 | 173 | 1.76 |

EXAMPLES 2 TO 4

The vapor-deposited, dark red layers of the compound of the formula A, prepared as in Example 1, are whirler-coated with solutions, in THF, of equal parts by weight of the hydrazone and pyrazoline compounds of formulas 1, 2, and 4, and of the binder of Example 1. The whirler-coated layers are then dried, and the light-sensitivity is measured for the about 9 to 10 μm thick layers.

| Compound | (−) $U_o$ (V) | (−) $U_R$ (V) | $E_{\frac{1}{2}}$ |
|---|---|---|---|
| 1 | 747 | 137 | 2.37 |
| 2 | 474 | 93 | 2.51 |
| 4 | 727 | 180 | 1.73 |

EXAMPLES 5 TO 9

A polyester film provided with an aluminum layer by vapor deposition is coated by vapor deposition with N,N'-bis-(3-methoxypropyl)-perylene-3,4,9,10-tetracarboxylic acid diimide (formula B) at about 180° to 220° C. under $10^{-7}$ to $10^{-8}$ bar in the course of 2 minutes. These conditions produce a bluish-green, stable modification of the compound, which absorbs light between 430 and 650 nm.

This homogeneously vapor-deposited layer weighing about 200 g/m$^2$ is whirler-coated with solutions in THF of equal parts by weight of the compounds of the formulae 1 to 4 and polycarbonate, and the whirler-coated layer is dried. The approximately 9 to 10 μm thick layers have the following light-sensitivities:

| Compound | (−) $U_o$ (V) | (−) $U_R$ (V) | $E_{\frac{1}{2}}$ |
|---|---|---|---|
| 1 | 713 | 186 | 1.62 |
| 2 | 687 | 153 | 1.71 |
| 3 | 740 | 180 | 1.46 |
| 4 | 800 | 226 | 1.37 |

If under otherwise identical experimental conditions the compound 2-(4'-diethylaminophenyl-4-chloro-5-(4'-methoxyphenyl)-1,3-oxazole, as described in German Pat. No. 1,120,875 (corresponding to U.S. Pat. No. 3,257,203), is used for comparison, the following values are obtained:

| (−) $U_o$ (V) | (−) $U_R$ (V) | $E_{\frac{1}{2}}$ |
|---|---|---|
| 620 | 206 | 2.04 |

If the charge transport layers described are replaced, for comparison, by a layer comprisng equal parts by weight of a polyester as a binder (Dynapol 206, Dynamit Nobel) and of the vinyloxazole mentioned in Example 1, under otherwise identical experimental conditions, the following values are obtained:

| $(-) U_o (V)$ | $(-) U_R (V)$ | $E_{\frac{1}{2}}$ |
|---|---|---|
| 620 | 200 | 3.04 |

EXAMPLES 10 TO 11

A polyester film provided with a vapor-deposited aluminum layer is coated, by vaporizing in a vacuum vaporizing unit, with the compound of the formula C, which absorbs light virtually in the whole visible range (420 to 750 nm), at a heating temperature of about 350° to 370° C. and under $8 \times 10^{-5}$ to $10^{-4}$ bar, in the course of about 2 to 3 minutes. The weight of the layer is then about 200 mg/m$^2$.

These violet vapor-deposited layers are then coated with about 9 to 10 μm thick layers of compounds of formulas 3 and 4 and polycarbonate as a binder as described in the above examples. The light-sensitivity measurement gives the following values:

| Compound | $(-) U_o (V)$ | $(-) U_R (V)$ | $E_{\frac{1}{2}}$ |
|---|---|---|---|
| 3 | 426 | 140 | 0.95 |
| 4 | 440 | 146 | 1.62 |

I claim:

1. An electrophotographic recording material comprising (i) an electrically conductive support, (ii) a charge generating layer comprising a diimide of perylenetetracarboxylic acid, and (iii) a charge-transporting layer comprising a polycarbonate binder and a compound of the formula

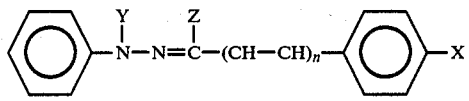

in which
  x is selected from the group consisting of methyl and methoxyl,
  n denotes zero or 1, and
  Y and Z together denote a grouping represented by the formula

A—CH—CH$_2$ where
  A is selected from the group consisting of phenyl and p-tolyl.

2. A recording material as in claim 1, wherein said diimide of perylenetetracarboxylic acid is N,N'-dimethylperylene-3,4,9,10-tetracarboxylic acid diimide.

3. A recording material as in claim 1, wherein said diimide of perylenetetracarboxylic acid is N,N'-bis-(3-methoxypropyl)-perylene-3,4,9,10-tetracarboxylic acid diimide.

4. A recording material as in claim 1, wherein said diimide of perylenetetracarboxylic acid is the condensation product of perylenetetracarboxylic anhydride and o-phenylenediamine.

5. A recording material as in claim 1, wherein said compound comprising said charge-transporting layer is 1,5-diphenyl-3-p-methoxyphenylpyrazoline.

6. A recording material as in claim 1, wherein said compound comprising said charge-transporting layer is 1-phenyl-3-p-methylstyryl-5-p-tolylpyrazoline.

7. A recording material as in claim 1, further comprising an insulating interlayer interposed between said support and said charge generating layer.

8. A recording material as in claim 1, wherein said diimide of perylenetetracarboxylic acid has been applied by vacuum vapor deposition.

9. A recording material as claimed in claim 1, wherein said charge generating layer further comprises a polycarbonate binder.

10. A recording material as claimed in claim 9, wherein said charge transport layer is interposed between said support and said charge generating layer.

11. A recording material as claimed in claim 10, wherein said diimide is dispersed in said polycarbonate binder.

* * * * *